United States Patent
Rudischhauser et al.

(10) Patent No.: US 6,676,598 B2
(45) Date of Patent: Jan. 13, 2004

(54) LARYNGOSCOPE

(75) Inventors: Jürgen Rudischhauser, Tuttlingen (DE); Martin Renner, Liptingen (DE); Klaus M. Irion, Liptingen (DE); Peter Schwarz, Tuttlingen (DE); Helmut Wehrstein, Tuttlingen (DE); Mark Kocher, Sindelfingen (DE)

(73) Assignee: Karl Storz GmbH & Co. KG (DE)

( * ) Notice: Subject to any disclaimer, the term of this patent is extended or adjusted under 35 U.S.C. 154(b) by 98 days.

(21) Appl. No.: 09/988,955

(22) Filed: Nov. 21, 2001

(65) Prior Publication Data
US 2002/0087050 A1 Jul. 4, 2002

Related U.S. Application Data

(63) Continuation of application No. PCT/EP00/04514, filed on May 18, 2000.

(30) Foreign Application Priority Data

May 21, 1999 (DE) .......................................... 199 23 334
Nov. 16, 1999 (DE) .......................................... 199 55 180

(51) Int. Cl.$^7$ ............................................. A61B 1/267
(52) U.S. Cl. ...................................................... 600/188
(58) Field of Search ................................. 600/185, 188, 600/189, 190, 191, 193, 197, 199, 200

(56) References Cited

U.S. PATENT DOCUMENTS

| | | | | |
|---|---|---|---|---|
| 3,592,199 A | * | 7/1971 | Ostensen | 600/199 |
| 4,306,547 A | * | 12/1981 | Lowell | 600/188 |
| 4,320,745 A | | 3/1982 | Bhitiyakul et al. | 128/11 |
| 4,517,964 A | * | 5/1985 | Upsher | 600/199 |
| 4,742,819 A | | 5/1988 | George | 128/6 |
| 4,877,016 A | | 10/1989 | Kantor et al. | 128/6 |
| 5,800,344 A | | 9/1998 | Wood, Sr. et al. | 600/188 |
| 5,827,178 A | | 10/1998 | Berall | 600/185 |
| 5,846,186 A | | 12/1998 | Upsher | 600/185 |
| 5,873,818 A | | 2/1999 | Rothfels | 600/188 |
| 5,879,289 A | | 3/1999 | Yarush et al. | 600/179 |
| 5,879,304 A | * | 3/1999 | Shuchman et al. | 600/193 |

FOREIGN PATENT DOCUMENTS

| | | |
|---|---|---|
| DE | 1766713 | 1/1971 |
| DE | 7528678 | 1/1976 |
| DE | 3431022 | 4/1986 |
| DE | 19715507 | 2/1999 |
| EP | 0901772 | 3/1999 |
| WO | WO98/19589 | 5/1998 |
| WO | WO 98/46117 | 10/1998 |

* cited by examiner

Primary Examiner—Cary E. O'Connor
(74) Attorney, Agent, or Firm—St. Onge Steward Johnston & Reens LLC

(57) ABSTRACT

A laryngoscope includes a handle, a spatula arranged substantially transverse to the handle, and a coupling detachably fixing the spatula to the handle. An illumination light waveguide guides an illumination light signal and an image waveguide guides an image signal, both waveguides being attached to the spatula. The illumination light waveguide includes a proximal end having an illumination light entry opening, and the image waveguide includes a proximal end having an image exit opening, wherein the illumination light entry opening and the image exit opening are arranged in the area of the coupling. The handle includes, in the area of the coupling, an illumination light exit opening and an image entry opening which allow for the illumination light signal to couple into the illumination light waveguide from the handle, and for the image signal to couple out of the image waveguide. A centering element automatically aligns the image entry opening and the image exit opening precisely to each other.

14 Claims, 8 Drawing Sheets

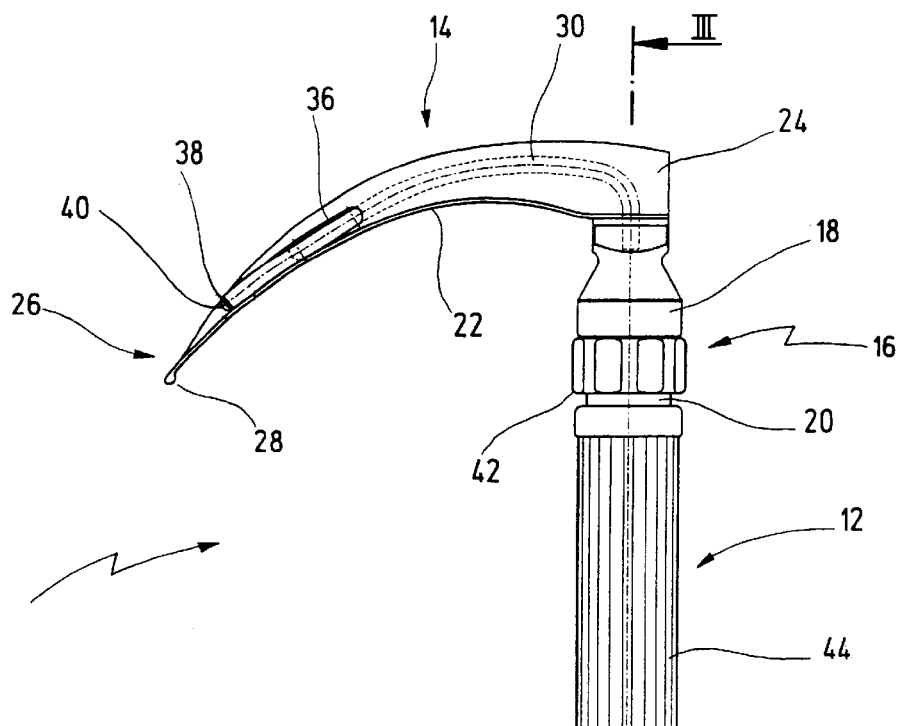
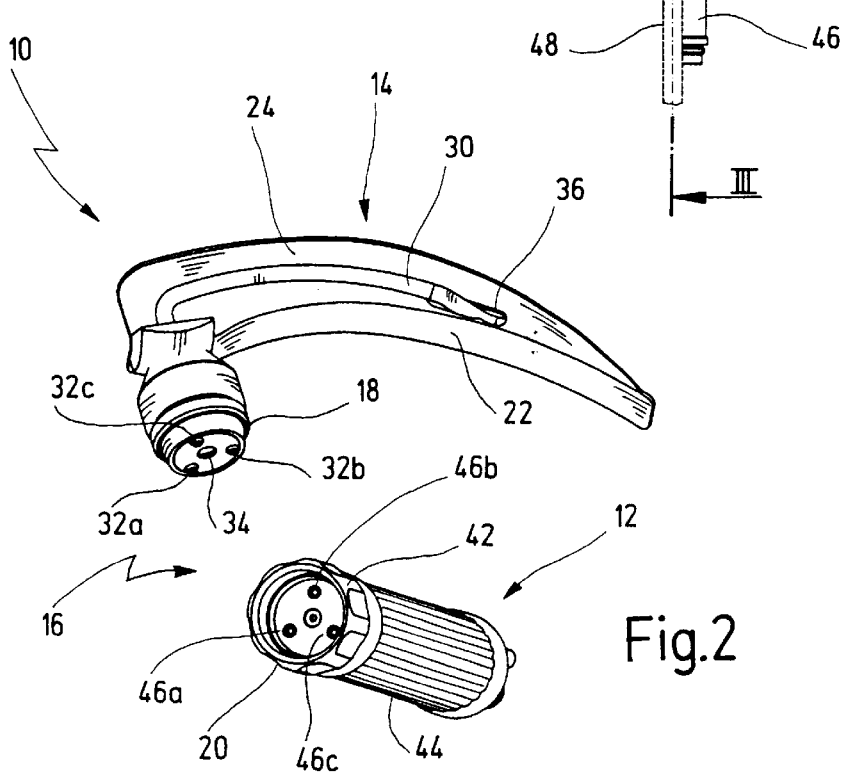
Fig.1
Fig.2

LARYNGOSCOPE

CROSSREFERENCE TO RELATED APPLICATION

This application is a continuation of pending international application PCT/EP00/04514 filed on May 18, 2000, and designating the U.S.

BACKGROUND OF THE INVENTION

The invention relates to a laryngoscope comprising a handle, a spatula arranged substantially transverse to said handle, and a coupling, wherein said spatula is detachably fixed to said handle by means of said coupling.

The invention relates specifically to such a laryngoscope further comprising an illumination light waveguide and an image waveguide, both of which being attached to said spatula, wherein said illumination light waveguide comprises a proximal end having an illumination light entry opening, and wherein said image waveguide comprises a proximal end having an image exit opening, wherein said illumination light entry opening and said image exit opening are arranged in the area of said coupling, and wherein said handle comprises, in the area of said coupling, an illumination light exit opening and an image entry opening which allow for an illumination light signal to couple from said handle into said illumination light waveguide, and for an image signal to couple out of said image waveguide.

A laryngoscope of that kind is generally known from EP 0 901 772 A1.

The image waveguide of the known laryngoscope, which might be designated as video-laryngoscope, serves for grabbing an image in the area of the distal end of said spatula, i.e. from a throat area of a patient, and for transmitting said image to an image displaying unit. The image displaying unit might be attached to the handle, but this is not necessary. In any case, however, the grabbed image signal has to be transferred over the separable coupling. This is achieved by coupling the image signal from the image waveguide arranged on the spatula into the image entry opening of an image grabbing system that is located in the handle.

Coupling an image signal from one image waveguide into another always causes losses in quality. As it has turned out, these losses are the less, the more exact the corresponding openings are aligned with respect to each other.

The laryngoscope known from EP 0 901 772 A1 comprises a catching fastener located in the region of the coupling, and ensuring that the laryngoscope spatula is connectable to an image grabbing unit, which is located in the handle, such that the region of the throat area, which is important for the operating physician, can always be imaged. However, any reduction of losses in quality as mentioned above is not guaranteed by this configuration, since the region which is important for the physician to be observed allows positional displacements in the range of several millimeters, whereas the image transmitting quality is already impaired at relative positional displacements of the two coupling openings in the range of several micrometers. Thus, a reduction of losses in quality requires a substantially higher positional accuracy.

From U.S. Pat. Nos. 5,846,186 and 5,800,344, video-laryngoscopes are known wherein the image waveguide is not led across the coupling, just in contrast to the laryngoscope mentioned at the outset. That is how losses in quality are avoided, since the image waveguide can be made in one piece. These laryngoscopes, however, complicate the handling for the physician due to the cables in the proximal region of the spatula.

It is therefore an object of the present invention to provide a laryngoscope of the type mentioned at the outset which provides for reduced losses in quality during image transfer, and which provides a simple handling at the same time.

SUMMARY OF THE INVENTION

This object is achieved with a laryngoscope as mentioned at the outset that comprises a centering element which automatically aligns the image entry opening and the image exit opening precisely to each other.

By means of such a centering element, a given adjustment of the coupling openings is not only fixed, but beyond that the absolute position of the coupling openings with respect to each other is guaranteed, in contrast to a catching fastener. From the technical point of view, displacement of the positions of the coupling openings is not only prevented after putting together the spatula and the handle, but, what is more, in putting together the handle and the spatula, an optimum alignment of the coupling openings is already attained. Thereby, the light entry opening and the light exit opening are always optimally arranged with respect to each other, and losses in quality are minimum when the image signal is coupled over.

Moreover, the laryngoscope according to this invention provides for the same easy handling as the laryngoscope mentioned at the outset. The object is therefore completely achieved.

In an embodiment of the invention, the centering element mechanically aligns said image entry opening and said image exit opening with respect to each other.

This feature provides for a simple and robust handling, in particular when connecting the spatula to the handle.

In a further embodiment, the centering element aligns the image entry opening and the image exit opening both in radial and in axial direction with respect to each other.

This feature is particularly advantageous with respect to the fact that not only a radial displacement of the openings allocated to each other, but also an axial displacement may cause deterioration in image quality. For attaining an optimum image quality, it is therefore advantageous to center the openings allocated to each other in every direction.

In a further embodiment, the centering element fixes said entry and exit openings with a variation in fitting of less than 0.5 mm, preferably less than 0.1 mm.

These dimensions have turned out to be advantageous in practical experiments in order to guarantee a constant image quality even during a rough handling of the laryngoscope, and during force impact, in particular in emergency situations.

In a further embodiment, the centering element comprises at least one cone and a corresponding counter cone, one of which being disposed at said handle and the other one at said spatula.

Such an embodiment has turned out to be particularly advantageous for the centering element, as it is simple and robust on the one hand, and it combines the advantageous features mentioned before on the other.

In a further embodiment, the centering element comprises an electronic image alignment unit.

In particular, an electronic image alignment unit can be realized by arranging an electronic image or frame grabber, e.g. a CCD-chip, in the handle of the laryngoscope, the light-sensitive, active area of which being larger than the area really required. In such a case, the electronic image or frame grabber is capable to catch the image signal transmitted by the image waveguide even, if the adjustment of the image entry and exit openings is not exactly maintained any more. By measures known per se from electronic image processing, the "true" image sector can be extracted then. The feature has the advantage, both if taken alone or in combination with a mechanical alignment element, that the image quality of the laryngoscope according to the invention can be constantly maintained, even if loads and forces are acting.

In a further preferred embodiment of the invention, the image entry opening and the illumination light exit opening are located in different coupling planes that are axially displaced with respect to each other.

This feature has the advantage that scattering of the illumination light signal into the image waveguide is prevented in a simple manner, whereby the image quality of the inventive laryngoscope is further improved.

In a further preferred embodiment, the coupling is a standard coupling for connecting laryngoscope-spatulas to handles.

In this connection, every coupling is considered as a standard coupling which has become so widespread among laryngoscopes that a considerable number of laryngoscopes operate with this coupling. The feature has the advantage that the spatulas and handles of the laryngoscopes being already in use can alternatively be combined with the spatula and the handle of the inventive laryngoscope, although the image displaying unit might not be used in this case. In an emergency situation, however, there is the possibility to combine any spatula more suitable with respect to its size with the handle of the inventive laryngoscope due to this feature. All in all, the application variety is enlarged due to the features mentioned.

In a further embodiment of the feature mentioned before, the coupling complies with the requirements of International Standard ISO 7376-3.

This standard defines a standard coupling for connecting spatulas and handles of laryngoscopes. Accordingly, numerous laryngoscopes operate with this standard coupling, and they benefit from the combination possibilities discussed before.

In a further embodiment of the features mentioned before, the coupling comprises, at the proximal end of the image waveguide, a coupling area which is located outside of the coupling area defined by International Standard ISO 7376-3.

Alternatively, it is basically feasible to integrate the proximal end of the image waveguide in the coupling within the dimensions determined by standard ISO 7376-3. In contrast thereto, the feature has the advantage that the region defined by the standard need not be modified, which considerably facilitates compliance with this standard. In addition, due to this feature, a second coupling region is provided which improves the stability and the support of the coupling. This is particularly advantageous with respect to the accuracy in fitting which has to be observed in positioning the entry and exit openings allocated to each other.

In a further embodiment of the invention, the laryngoscope comprises an image displaying unit located at the handle in order to display a grabbed image.

This feature makes the inventive laryngoscope autonomous, i.e. it may be used independently of an external monitor or any other external devices. In that way, handling and expenditure, in particular with respect to emergency situations, is considerably facilitated.

In a further embodiment of the feature mentioned before, the image displaying unit is located on a side of the handle facing away from the distal end of the spatula.

This feature has the advantage that the operating physician can observe the image supplied by the image displaying unit virtually from behind, i.e. from the reverse side of the laryngoscope. This is particularly favorable, since the operating physician thus can quickly switch between the image supplied by the image displaying unit and a direct glance into the throat area of the patient, without having to turn his head a lot.

In a further embodiment, the image displaying unit is rotatable around a longitudinal axis of the handle.

This feature has the advantage that the operating physician can easily adjust the alignment of the image displaying unit to his needs. Moreover, a rotation of the image displaying unit about the longitudinal axis of the handle can be realized in a more robust way than a rotation about an axis that is orthogonal to the longitudinal axis of the handle. The laryngoscope of this embodiment is therefore very robust, in spite of the additional possibility of adjusting.

In a further embodiment, the image displaying unit can be tilted with respect to the longitudinal axis of the handle.

This feature also has the advantage that the operating physician can adjust the alignment of the image displaying unit to his needs while using the laryngoscope.

In a further embodiment, the image displaying unit can be separated from the handle.

This feature has the advantage that the image displaying unit can easily be exchanged in case of damage. Another advantage is that the operating physician may remove the image displaying unit from the handle, if he does not need it any longer for the treatment of a patient. In this case, the inventive laryngoscope corresponds to any common laryngoscope without an image displaying unit with respect to its dimensions and its handling.

In a further embodiment, at least a part of the spatula is made of a light guiding material which forms the illumination light waveguide.

This feature has the advantage that additional optical fibers for the illumination light waveguides might be omitted. In that way, robustness of the laryngoscope can be further improved, while production costs can be saved at the same time. In addition, a light exit for illuminating the throat area can be arranged in a simple way at the distal end of the spatula, without the need to change the function-dependent shape of the spatula.

In a further embodiment, the laryngoscope comprises at least two image waveguides and two image grabbing units.

This feature has the advantage that a stereoscopic and, thus, a spatial image can be achieved which further facilitates the orientation for the operating physician when intubating a patient.

In a further embodiment, a gas sensor for measuring parameters of a gas mixture is arranged at the distal end of the spatula.

The gas sensor preferably serves for determining the oxygen content and/or the $CO_2$ content. The measure is particularly advantageous when the laryngoscope is used in emergency situations for intubating an asphyxiating patient. In such a situation, the amount of oxygen can be determined in the region of the trachea entrance in a simple manner.

In a further embodiment of the feature mentioned before, the gas sensor is connected to an evaluation unit arranged in the handle.

This feature has the advantage that the relatively delicate evaluation unit is protected in the laryngoscope. Furthermore, the laryngoscope provides for the possibility to use the signals of the gas sensor without external devices.

It is to be understood that the features mentioned above and those to be explained below are not only applicable in the given combinations, but may also be used in different combinations or taken alone without departing from the scope of the present invention.

BRIEF DESCRIPTION OF THE DRAWINGS

The invention will be described in more detail below in conjunction with selected embodiments and the drawings referred to in the following:

FIG. 1 shows a first embodiment of a laryngoscope according to the invention in a side view;

FIG. 2 shows the laryngoscope of FIG. 1 in a perspective view, wherein the spatula is separated from the handle;

DETAILED DESCRIPTION OF PREFERRED EMBODIMENTS

Figure 3:
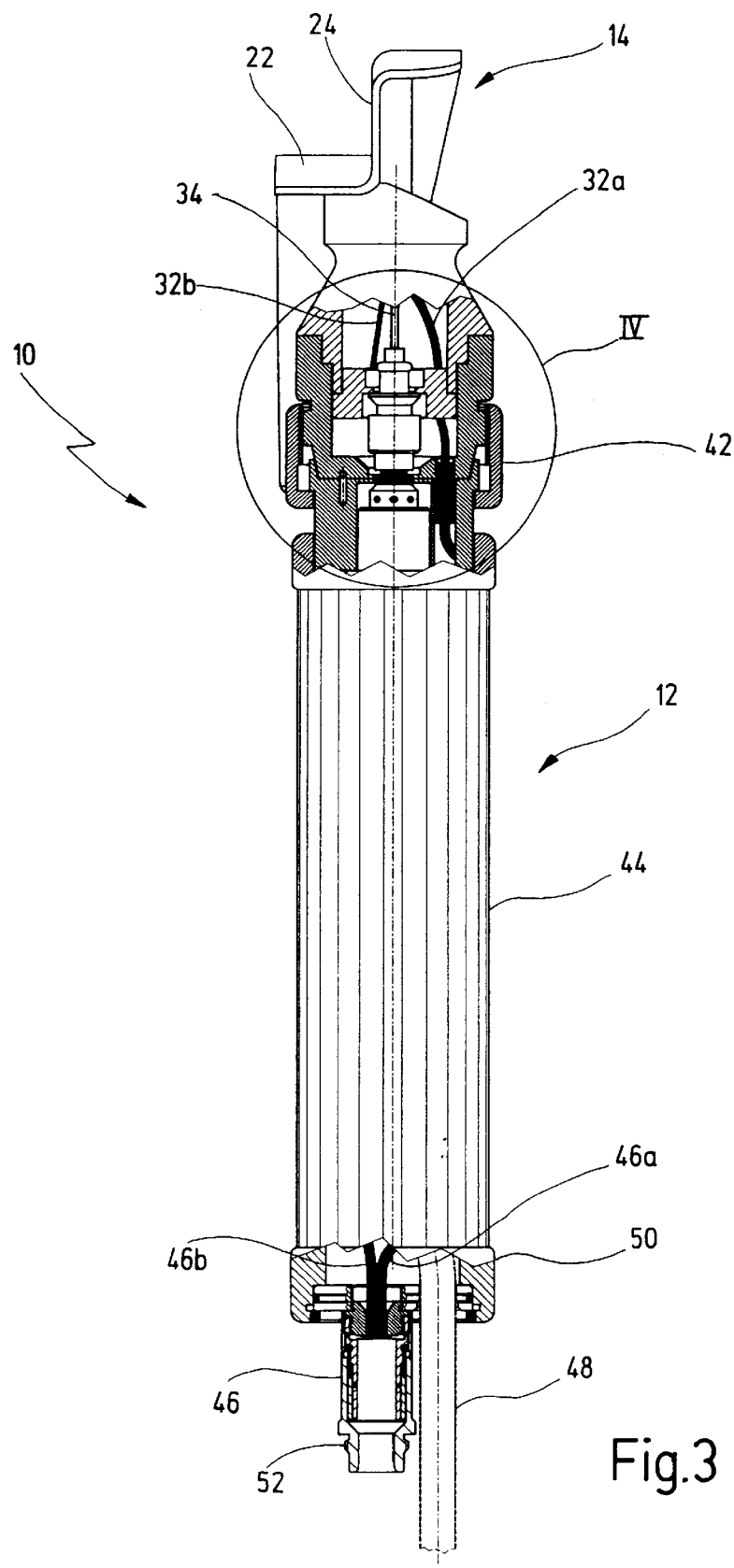
FIG. 3 shows the laryngoscope of FIG. 1 along line III—III.

In FIGS. 1 to 3 a laryngoscope according to the invention is designated in its entirety with reference numeral 10.

Laryngoscope 10 comprises a handle 12 and a spatula 14 which are connected to each other by means of a coupling 16. The spatula-sided part of coupling 16 is designated with reference numeral 18 and the handle-sided part with reference numeral 20.

In a way known per se, spatula 14 comprises a spatula blade 22, a lateral wall 24 of which projects substantially vertically upwards. At its distal end 26, spatula blade 22 comprises a bead 28. On that side of lateral wall 24 that faces away from spatula blade 22, a tube 30 is laid which accommodates both an illumination light waveguide 32 and an image waveguide 34. In the present embodiment, illumination light waveguide 32 comprises three individual illumination light waveguide strings 32a, 32b, 32c which are radially arranged around image waveguide 34, as can be seen in opened coupling 16 in FIG. 2.

Tube 30 extends on the reverse side of lateral wall 24 to an oblong hole 36 and emerges through lateral wall 24 onto spatula blade 22. At the distal end of tube 30, illumination light waveguide 32 comprises a light exit opening 38. Image waveguide 34 comprises an image entry opening 40 there. The combined arrangement of illumination light waveguide 32 and image waveguide 34 in a tube 30 is known per se in the prior art and, thus, needs not to be explained in more detail.

Coupling 16 of laryngoscope 10 is a bayonet-like coupling with parts 18, 20 to be connected being fixed by a retaining nut 42. Further details of the coupling are described in the following with respect to FIGS. 4 and 5.

Handle 12 of laryngoscope 10 comprises in a manner known per se a tube-shaped shaft 44 which accommodates further components of laryngoscope 10. In this specific embodiment, two external cable connections 46, 48 belong to these components, as can be seen in FIG. 3. At the upper end in FIGS. 4 and 5 cable connection 48 comprises an image grabbing module 49 that transforms a received image signal into an electric image signal.

A light signal can be supplied to laryngoscope 10 via cable connection 46, which comprises a plug contact 52 at the bottom end 50 of handle 12. On the other hand, cable connection 48 serves for transmitting the optical image signal of an image taken at image entry opening 40 in the form of an electric image signal to an image displaying unit that is not shown herein.

In the cross sectional view of FIG. 3, it is further to be seen that cable connection 46 splits, in the inner part of handle 12, into three individual strings 46a, 46b and 46c which adjoin to the individual strings of illumination light waveguide 32 in the region of coupling 16 (cf. FIG. 2).

Figure 4:
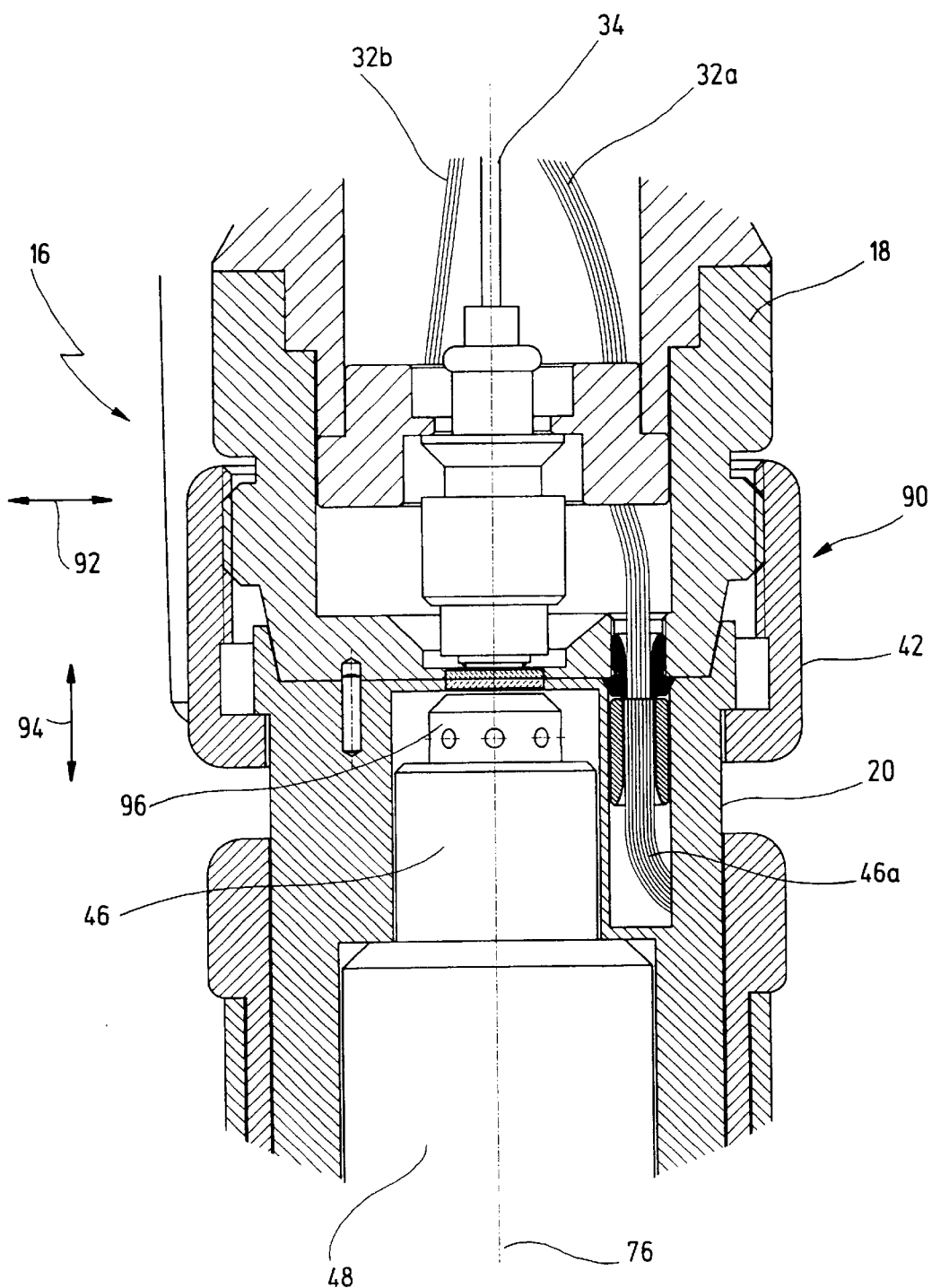
FIG. 4 shows the coupling of the laryngoscope of FIG. 3 in a detailed view.
Figure 5:
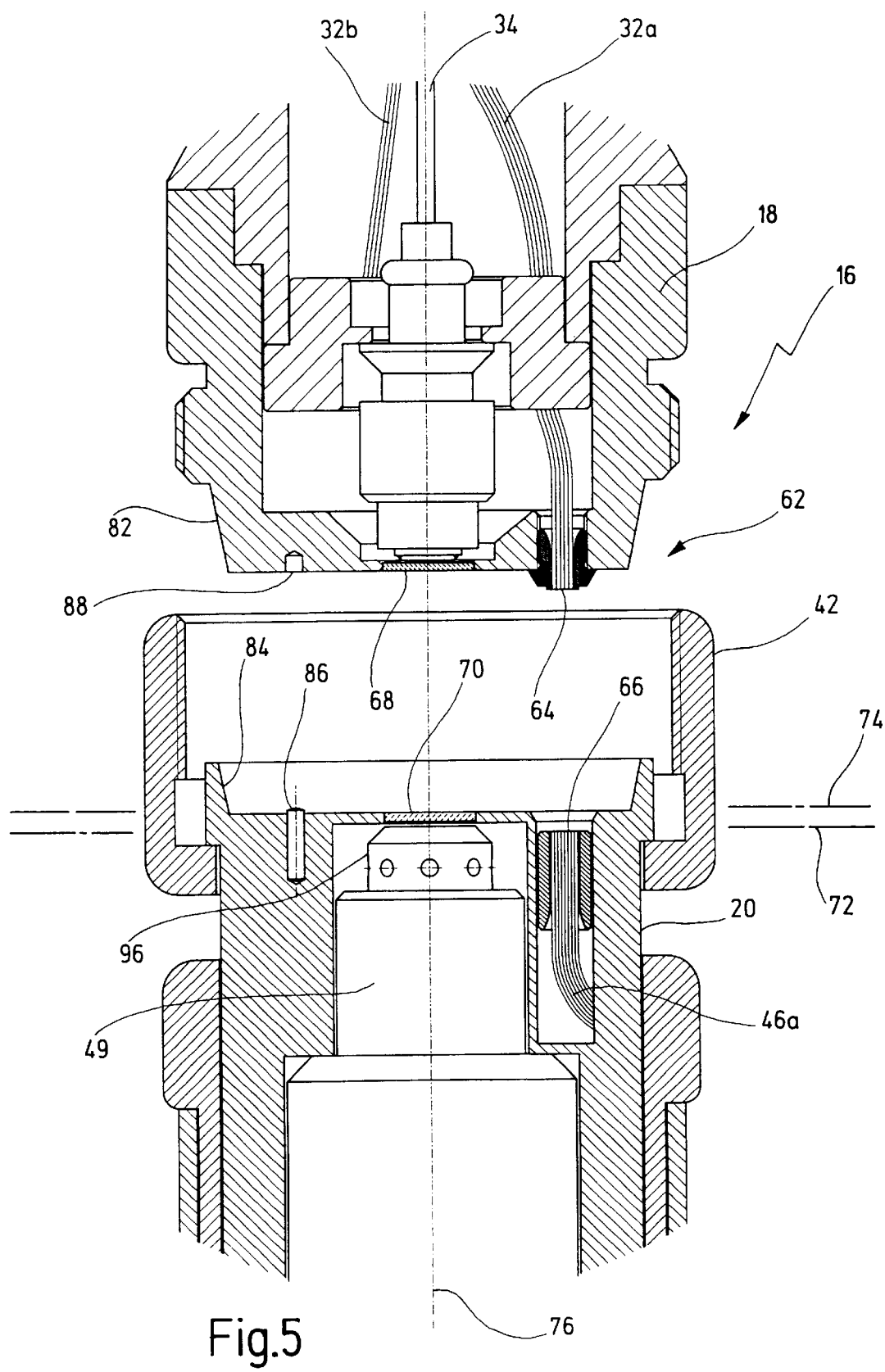
FIG. 5 shows the coupling of FIG. 4, wherein the spatula and the handle are separated from each other.

In the enlarged cross sectional view of FIGS. 4 and 5, only strings 32a and 32b of illumination light waveguide 32 as well as string 46a of cable connection 46 can be seen. Just like remaining strings 32b, 32c, string 32a of illumination light waveguide 32 comprises a light entry opening 64 at its bottom end 62, which is also referred to as proximal end in the following. In the handle-sided part 20 of laryngoscope 10 and opposite from light entry opening 64, light exit opening 66 of string 46a of cable connection 46 is located. When spatula 14 is connected to handle 12, as shown in FIG. 4, light entry opening 64 and light exit opening 66 are directly opposite to each other.

In a same way, image waveguide 34 comprises an image exit opening 68 at its proximal end 62, which is opposite from image entry opening 70 of image grabbing module 49. Entry and exit openings 64 to 70 are sealed by a cover glas in order to prevent dirt or dust from entering.

As particularly can be seen in the illustration of FIG. 5, light exit opening 66 and image entry opening 70 are arranged in two different coupling planes 72, 74 which are axially displaced with respect to each other along longitudinal center axis 76 of handle 12, this prevents scattering light created in the region of light exit opening 66 to enter through image entry opening 70 into the image section. In a same way, light entry opening 64 and image exit opening 68 are arranged in different planes that are axially displaced with respect to each other.

Illumination light waveguide 32 and image waveguide 34 solely consist of optical fiber bundles in the present embodiment of laryngoscope 10. In particular image waveguide 34, however, may also comprise a lens system, alternatively hereto.

Beside retaining nut 42 the mechanical part of coupling 16 particularly comprises a cone 82 at proximal end 62 of spatula 14, and a corresponding counter cone 84 at the upper end of handle 12. Furthermore, an orientation pin 86 is provided which has to be introduced into a suitable bore 88 when spatula 14 is connected to handle 12. Orientation pin 86 ensures that spatula 14 can be put onto handle 12 only in a way such that entry and exit openings 64 to 70 are facing each other in a precisely fitting manner. In combination with retaining nut 42, these elements form a centering element 90 which ensures that corresponding entry and exit openings 64 to 70 are rigidly fixed to each other with an inaccuracy in fitting of less than 0.1 mm, both in radial direction (arrow 92) and in axial direction (arrow 94).

Image grabbing module 49 includes a magnification optic 96 that enlarges the optical image signal entering through image entry opening 70 by the factor 1:5 approximately and, subsequently, supplies the optical image signal to an electronic image or frame grabber that is not shown herein. In the present case the electronic image or frame grabber is a CCD-chip which transforms the optical image signal into an electrical image signal. However, any other electronic image grabber may be used herein. The CCD-chip further comprises means to carry out an electronic image centering in addition to mechanical centering element 90, according to a specifically preferred embodiment of the invention. This is particularly achieved by the CCD-chip comprising a larger active area than required, thereby the relevant image portion can be extracted by means of known image processing methods, if image exit opening 68 and image entry opening 70 are not optimally positioned with respect to each other due to forces acting onto laryngoscope 10.

In the following description of the further embodiments of the invention, same reference numerals designate same elements as in FIGS. 1 to 5.

Figure 6:
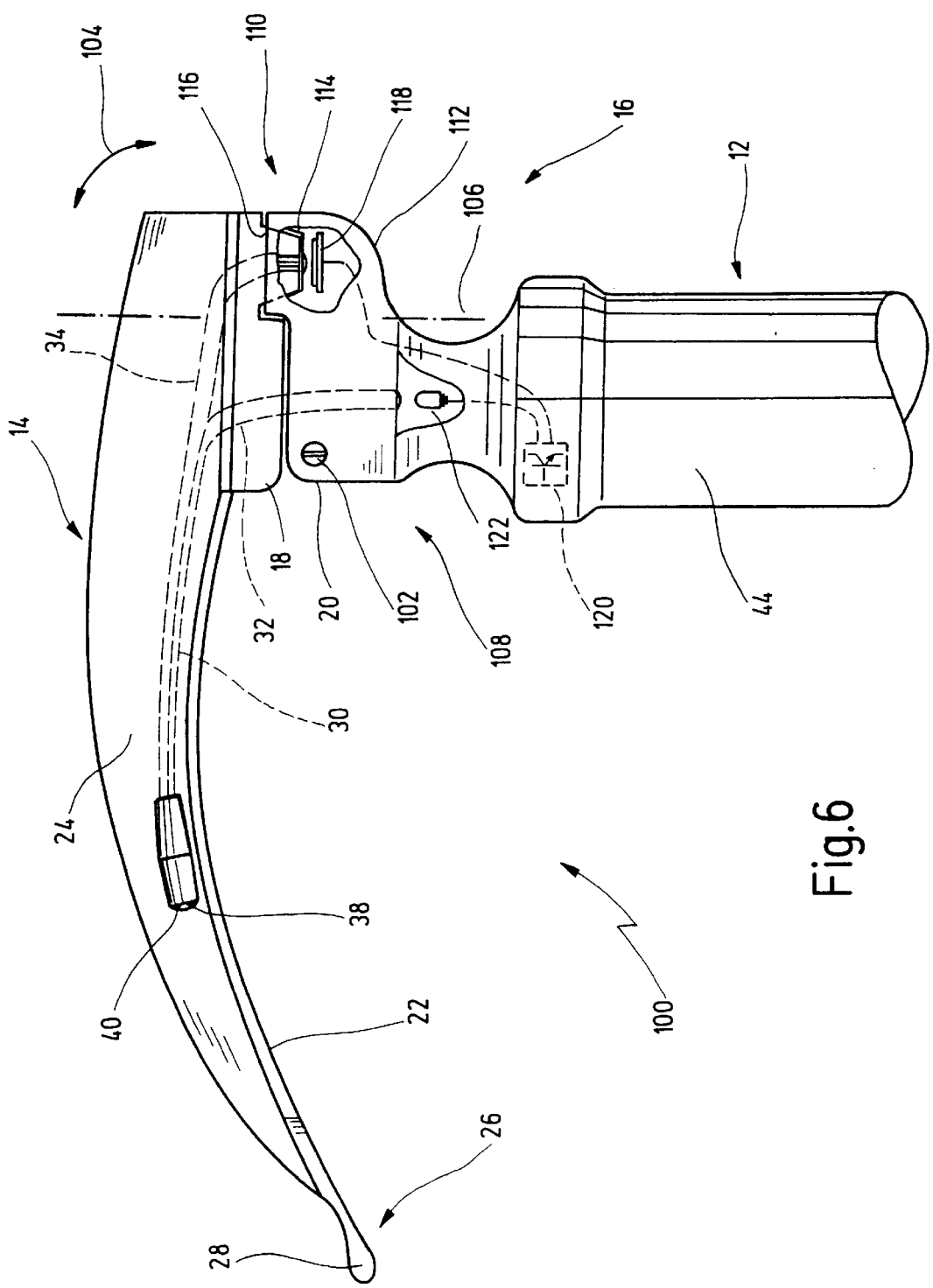
FIG. 6 shows a second embodiment of a laryngoscope according to the invention in a side view.

In FIG. 6, a second embodiment of a laryngoscope according to the invention is designated in its entirety with reference numeral 100.

Laryngoscope 100 differs from laryngoscope 10 in particular with respect to coupling 16 which is here a standard coupling complying with International Standard ISO 7376-3. This type of coupling has a transverse pin 102 which is located at the handle-sided part 20 of coupling 16. Spatula-sided part 18 comprises an U-shaped recess not recognizable in this view, by means of which spatula 14 can be put onto transverse pin 102. Spatula 14 can be pivoted about transverse pin 102 into the direction of arrow 104, thus facilitating assembling and disassembling of laryngoscope 100.

In order to prevent an unintended pivoting movement along the direction of arrow 104 during use of laryngoscope 100, locking elements (not to be seen in this view) are provided in the inner part of coupling 16.

Standard ISO 7376-3 defines only the part of coupling 16 that is located left from line 106 in FIG. 6. This coupling area is designated with the reference numeral 108 in the following. In this embodiment, at the right from line 106, an additional coupling area 110 is located, and the contact region of coupling 16 is enlarged by this area with respect to standard ISO 7376-3. According to a preferred embodiment, additional coupling area 110 is here arranged diametrically opposed from the distal end 26 of spatula 14.

In this embodiment, additional coupling area 110 accommodates the coupling for image waveguide 34. As a result, handle 12 of laryngoscope 100 can also be connected to any standard spatula not including an image waveguide, since such a standard spatula reaches only until line 106. In the same way, spatula 14 can be connected to any handle of a standard laryngoscope, the handle-sided part 20 of which not including coupling area 110.

In the present embodiment, coupling area 110 comprises a flange 112 at the handle-sided part 20 which has an inner cone 114 at its upper end. Spatula-sided part 18 has a suitable outer cone 116. Like in the previous embodiment, inner cone 114 and outer cone 116 are components of a centering element 90 that fixes the entry and exit openings 64 to 70 in their predetermined positions with respect to each other, in addition to suitable locking means not shown herein. For ease of illustration, reference numerals mentioned at last are not drawn in FIG. 6.

In case the locking means provided for standard coupling 16 should not be sufficient to rigidly ensure the required accuracy in fitting, further locking means may be added, which are also arranged in coupling area 110 preferably. Preferably, a retaining nut is used similar to that shown in FIG. 1, or any another locking mechanism that can be released only by hand.

In the partly sectioned view of coupling area 110, an electronic image grabber in form of a CCD-chip is to be seen. Its signals are supplied to an evaluation and control unit which is also arranged in handle 12 of laryngoscope 100. In the handle-sided part 20, laryngoscope 100 additionally accommodates a light source 122, the light of which is directly coupled into illumination light waveguide 32.

Beside that, laryngoscope 100 operates the same way as laryngoscope 10.

Figure 7:
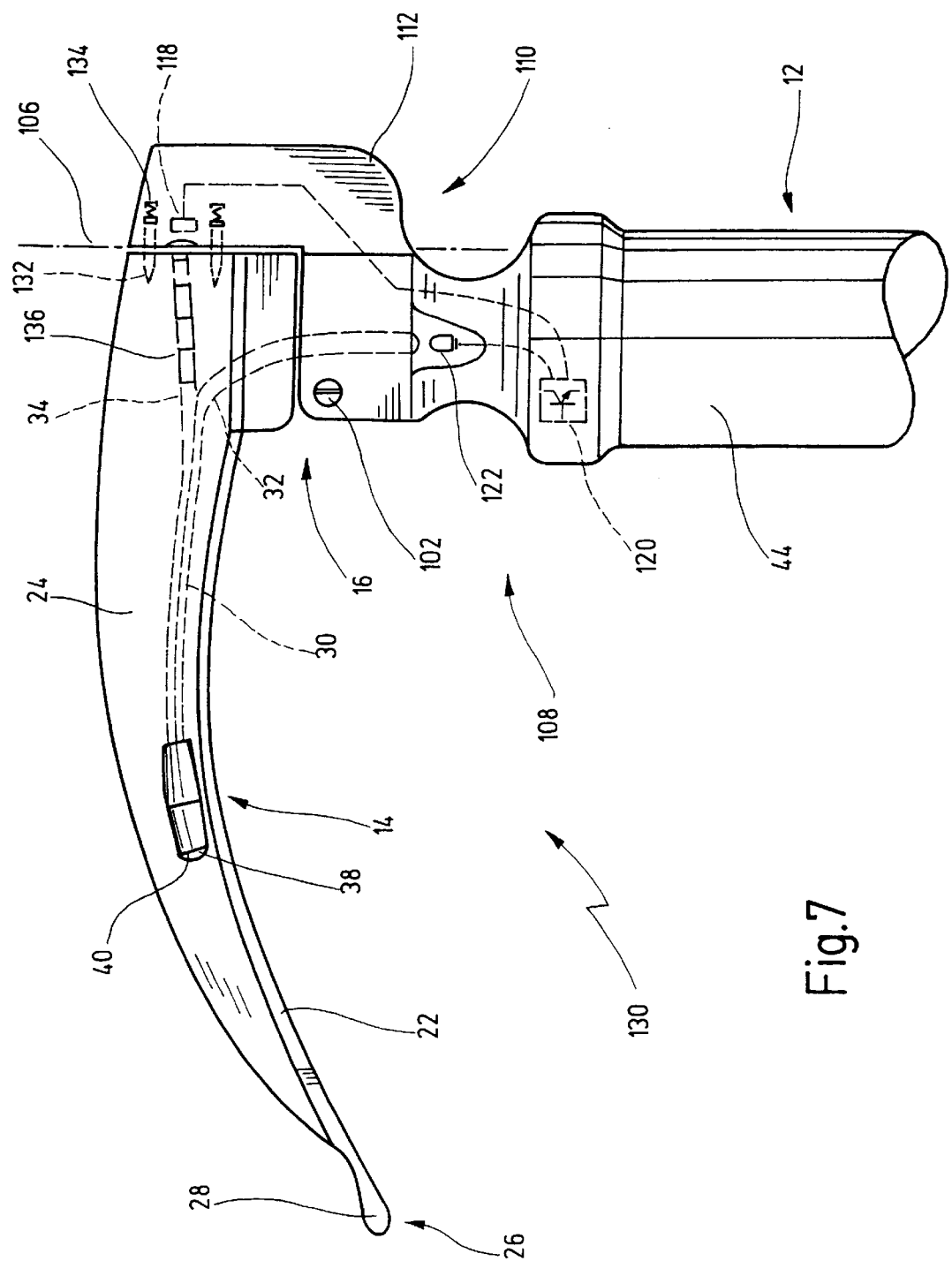
FIG. 7 shows a third embodiment of a laryngoscope according to the invention.

In the embodiment according to FIG. 7, a laryngoscope according to the invention is designated in its entirety with reference numeral 130.

Laryngoscope 130 substantially differs from laryngoscope 100 of FIG. 6 by a different kind of extension of standard coupling 16. However, the differences are limited to additional coupling area 110. The part of coupling 16 being left from line 106 in FIG. 7 completely complies with standard ISO 7363-3.

In laryngoscope 130, the electronic image grabber is arranged in a flange 112 that extends to the upper proximal end of spatula 14 in axial direction of handle 12. Spatula 14 is centered onto flange 112 by conic alignment pins 132 which engage in suitable conical shaped recesses at lateral wall 24 of spatula 14. Alignment pins 132 are mounted on springs 134, such that a spatula without recesses can push back alignment pins 132. Therefore, it is possible to use any standard spatula in connection with laryngoscope 130.

Since image waveguide 34 of laryngoscope 130 extends in a far less curved manner, it is possible here to use an image waveguide 34 that includes a lens system 136. Besides that, the function mode of laryngoscope 130 corresponds to that of laryngoscope 100.

Further embodiments of the invention are attained if features of the embodiments shown before by way of example are combined with each other. For instance, it is feasible to implement an internal light source 122 into laryngoscope 10. On the other side, laryngoscopes 100, 130 may be provided with a cable connection 46 for supplying illumination light from an outside light source. Likewise, laryngoscopes 100, 130 may be provided with an electronic image alignment unit.

In further embodiments, laryngoscopes comprise an image displaying unit directly fixed to or even integrated into handle 12 of the laryngoscope rather than a cable connection 48. In such a case, a completely autonomous video-laryngoscope is attained without external cable connections.

Figure 8:
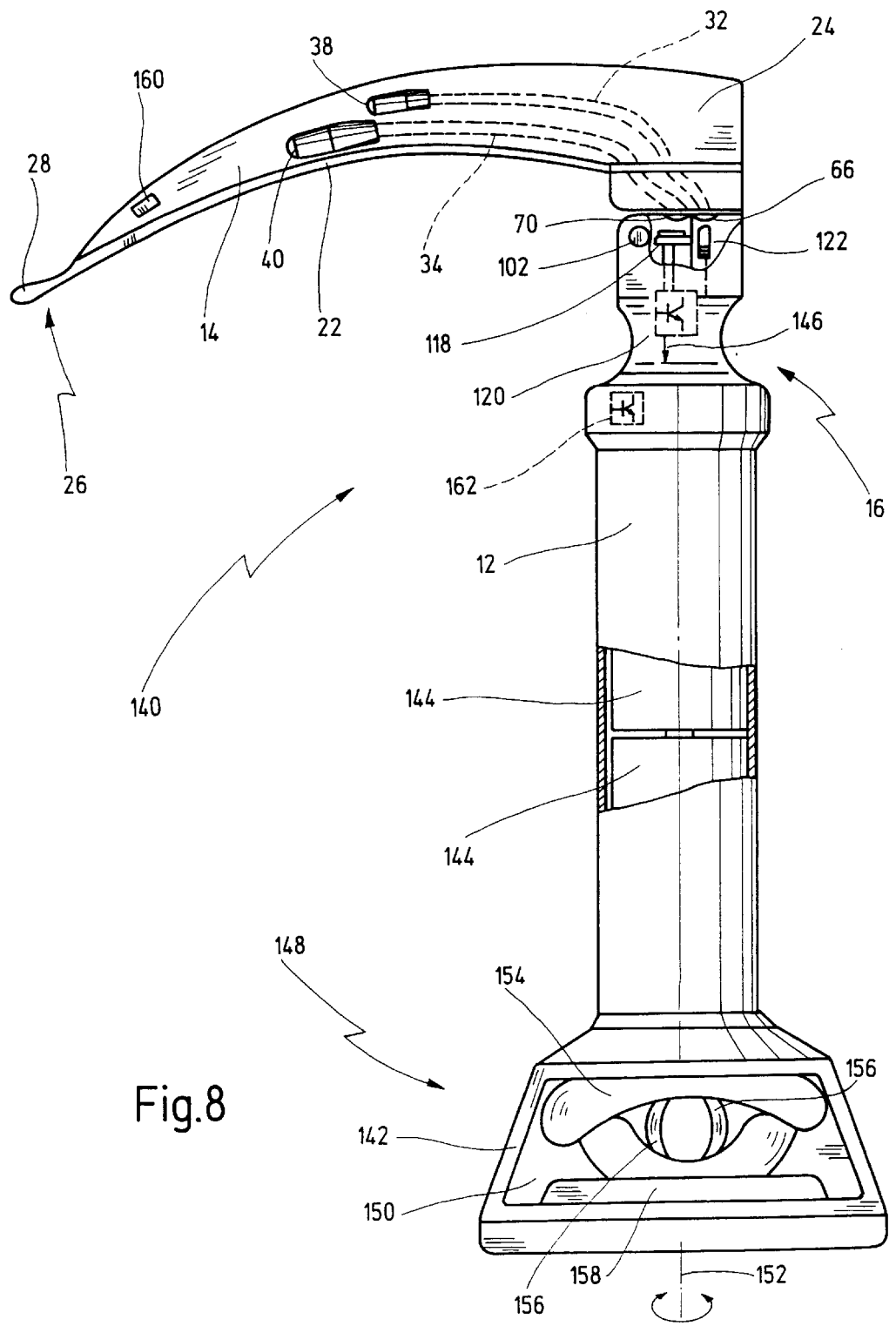
FIG. 8 shows an embodiment of an autonomous video-laryngoscopes.

In FIG. 8, such an autonomous video-laryngoscope is designated in its entirety with reference numeral 140.

For electrical power supply of image grabbing unit 118, light source 122, evaluation and control unit 120, and image displaying unit 142 explained in the following, two batteries 144 are accommodated in handle 12. Batteries 144 are electrically connected to the components mentioned above, which is indicated by arrow 146. Batteries 144 can be charged inductively here, i.e. remotely from outside.

At proximal end 148 of handle 12, an image displaying unit 142 is integrated comprising essentially a screen 150 that is visible for the operating physician. Screen 150 is made in LCD-technology in a sandwich arrangement, and colored. The whole image displaying unit 142 is rotatable around longitudinal axis 152 of handle 12, such that the operating physician can adapt the position of screen 150 according to his needs.

For illustration purposes, an image of the larynx area of a patient with epiglottis 154 and vocal cords 156 taken via image waveguide 34 and image grabbing unit 118, and reproduced via image displaying unit, is schematically shown on screen 150. Likewise, an image 158 of bead 28 at the distal end 26 of spatula 14 is to be seen in the display here.

In the embodiment shown here, image displaying unit 142 is detachable from proximal end 148 of handle 12. This is necessary in the present embodiment to change batteries 144, and, apart from that, might be favorable when image displaying unit 142 is not required. In a normal application, however, image displaying unit 142 will be fixed to handle 12.

Furthermore, the laryngoscope of this embodiment comprises a gas sensor 160 known per se which is arranged at distal end 26 of spatula 14. Due to gas sensor 160, it is possible to determine the oxygen content and/or the $CO_2$-content in the throat area of the patient. Gas sensor 160 is connected to an evaluation unit 162 that is arranged in handle 12.

In addition, laryngoscope 140 may be provided with an irrigation system not shown herein, by means of which a liquid, e.g. a NaCl-solution, may be led to distal end 26 of spatula 14 via handle 12 in order to clean the ends of illumination light waveguide 32 and image waveguide 34 during application.

Figure 9:
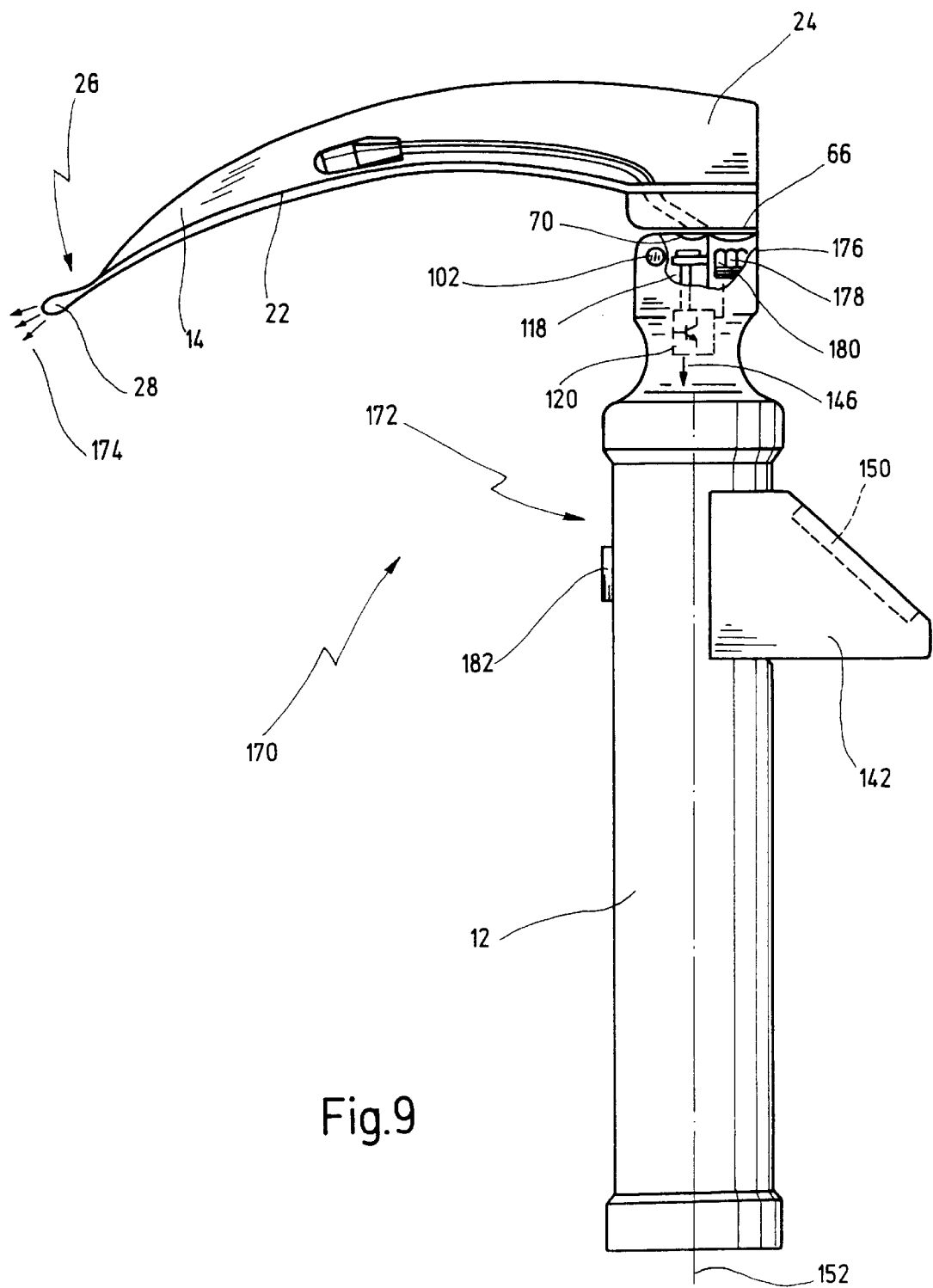
FIG. 9 shows a second embodiment of an autonomous video-laryngoscopes.

In FIG. 9, a further embodiment of an autonomous video-laryngoscope is designated in its entirety with reference numeral 170.

Laryngoscope particularly differs from the previous embodiment with respect to image displaying unit 142 which is rigidly fixed at distal end 172 of handle 12 here. In order to provide the operating physician with a good view onto screen 150, image displaying unit 142 is arranged on the side of handle 12 that faces away from distal end 26 of spatula 14. In an alternative embodiment not shown herein, screen 150 can be tilted with respect to longitudinal axis 152 of handle 12.

A further characteristic of laryngoscope 170 is spatula 14 consisting of a transparent, light-conducting material, e.g. plexiglass in the present case. The material is selected such that spatula blade 22 of spatula 14 replaces the illumination light waveguide. Accordingly, laryngoscope 170 operates with a single optical fiber for image waveguide 34 only. As indicated by arrows 174 in FIG. 9, light is conducted to distal end 26 of spatula 14, and it emerges there from bead 28.

As a further difference with respect to the previous embodiments, laryngoscope 170 here includes three different-colored light sources in form of three LEDs which are designated by reference numerals 176, 178, 180, and which cover the colors red, green, and blue.

Furthermore, at its handle 12 laryngoscope 170 comprises a jack 182 with electric connections for additional electric supply from outside, and for tapping signals supplied from image grabber 118 to image displaying unit 142. Thus, it is possible to telemetrically display the image from image grabber 118 on an external monitor. This might be carried out both in addition and alternatively to displaying the image on screen 150 of image displaying unit 142. In addition, jack 182 includes contacts for an external light source and, if applicable, for a telemetric evaluation of signals of a gas sensor 160.

In a special mode of operation of laryngoscope 170, light sources 176 to 180 are pulsed synchronically with an image frequency of image grabber 118, or image displaying unit 142, respectively, in order to reduce average power consumption.

What is claimed is:

1. A laryngoscope, comprising:
   a handle;
   a spatula arranged substantially transverse to said handle; and
   a coupling, wherein said spatula is detachably fixed to said handle by means of said coupling;
   an illumination light waveguide for guiding an illumination light signal and an image waveguide for guiding an image signal, both of said waveguides being attached to said spatula;
   wherein said illumination light waveguide comprises a proximal end having an illumination light entry opening, and wherein said image waveguide comprises a proximal end having an image exit opening, wherein said illumination light entry opening and said image exit opening are arranged in an area of said coupling;
   wherein said handle comprises, in said area of said coupling, an illumination light exit opening and an image entry opening which allow for said illumination light signal to couple into said illumination light waveguide from said handle, and for said image signal to couple out of said image waveguide;
   wherein said laryngoscope further comprises a centering element which automatically aligns said image entry opening and said image exit opening precisely to each other; and
   wherein said centering element comprises an electronic image alignment unit.

2. The laryngoscope of claim 1, wherein said coupling is a standard coupling for connecting laryngoscope-spatulas with handles.

3. The laryngoscope of claim 2, wherein said coupling complies with the requirements of International Standard ISO 7376-3.

4. The laryngoscope of claim 1, further comprising an image displaying unit for displaying an image guided through said image waveguide, said image displaying unit being located at said handle.

5. The laryngoscope of claim 4, wherein said handle has a longitudinal axis, and said image displaying unit is rotatable around said longitudinal axis.

6. The laryngoscope of claim 4, wherein said handle has a longitudinal axis, and said image displaying unit is capable of being tilted with respect to said longitudinal axis.

7. The laryngoscope of claim 4, wherein said image displaying unit is detachable from said handle.

8. The laryngoscope of claim 1, wherein said spatula is at least partly made of a light guiding material which forms said illumination light waveguide.

9. A laryngoscope, comprising:
   a handle;
   a spatula arranged substantially transverse to said handle; and
   a coupling, wherein said spatula is detachably fixed to said handle by means of said coupling;

an illumination light waveguide for guiding an illumination light signal and an image waveguide for guiding an image signal, both of said waveguides being attached to said spatula;

wherein said illumination light waveguide comprises a proximal end having an illumination light entry opening, and wherein said image waveguide comprises a proximal end having an image exit opening, wherein said illumination light entry opening and said image exit opening are arranged in an area of said coupling;

wherein said handle comprises, in said area of said coupling, an illumination light exit opening and an image entry opening which allow for said illumination light signal to couple into said illumination light waveguide from said handle, and for said image signal to couple out of said image waveguide;

wherein said laryngoscope further comprises a centering element which automatically aligns said image entry opening and said image exit opening precisely to each other; and wherein said image entry opening is located in a first coupling plane, and said illumination light exit opening is located in a second coupling plane, said first and second coupling planes being axially displaced with respect to each other.

10. A laryngoscope, comprising:

a handle;

a spatula arranged substantially transverse to said handle; and a coupling, wherein said spatula is detachably fixed to said handle by means of said coupling;

an illumination light waveguide for guiding an illumination light signal and an image waveguide for guiding an image signal, both of said waveguides being attached to said spatula;

wherein said illumination light waveguide comprises a proximal end having an illumination light entry opening, and wherein said image waveguide comprises a proximal end having an image exit opening, wherein said illumination light entry opening and said image exit opening are arranged in an area of said coupling;

wherein said handle comprises, in said area of said coupling, an illumination light exit opening and an image entry opening which allow for said illumination light signal to couple into said illumination light waveguide from said handle, and for said image signal to couple out of said image waveguide;

wherein said laryngoscope further comprises a centering element which automatically aligns said image entry opening and said image exit opening precisely to each other;

wherein said coupling is a standard coupling for connecting laryngoscope-spatulas with handles; and wherein said coupling comprises a coupling area located at said proximal end of said image waveguide, said coupling area being disposed outside of any coupling area defined by said International Standard ISO 7376-3.

11. A laryngoscope, comprising:

a handle;

a spatula arranged substantially transverse to said handle; and a coupling, wherein said spatula is detachably fixed to said handle by means of said coupling;

an illumination light waveguide for guiding an illumination light signal and an image waveguide for guiding an image signal, both of said waveguides being attached to said spatula;

wherein said illumination light waveguide comprises a proximal end having an illumination light entry opening, and wherein said image waveguide comprises a proximal end having an image exit opening, wherein said illumination light entry opening and said image exit opening are arranged in an area of said coupling;

wherein said handle comprises, in said area of said coupling, an illumination light exit opening and an image entry opening which allow for said illumination light signal to couple into said illumination light waveguide from said handle, and for said image signal to couple out of said image waveguide;

wherein said laryngoscope further comprises a centering element which automatically aligns said image entry opening and said image exit opening precisely to each other;

an image displaying unit for displaying an image guided through said image waveguide, said image displaying unit being located at said handle; and wherein said spatula includes a distal end, and wherein said image displaying unit is located on a side of said handle facing away from said distal end of said spatula.

12. A laryngoscope, comprising:

a handle;

a spatula arranged substantially transverse to said handle; and a coupling, wherein said spatula is detachably fixed to said handle by means of said coupling;

an illumination light waveguide for guiding an illumination light signal and an image waveguide for guiding an image signal, both of said waveguides being attached to said spatula;

wherein said illumination light waveguide comprises a proximal end having an illumination light entry opening, and wherein said image waveguide comprises a proximal end having an image exit opening, wherein said illumination light entry opening and said image exit opening are arranged in an area of said coupling;

wherein said handle comprises, in said area of said coupling, an illumination light exit opening and an image entry opening which allow for said illumination light signal to couple into said illumination light waveguide from said handle, and for said image signal to couple out of said image waveguide;

wherein said laryngoscope further comprises a centering element which automatically aligns said image entry opening and said image exit opening precisely to each other; and at least two image grabbing units.

13. A laryngoscope, comprising:

a handle;

a spatula arranged substantially transverse to said handle; and a coupling, wherein said spatula is detachably fixed to said handle by means of said coupling;

an illumination light waveguide for guiding an illumination light signal and an image waveguide for guiding an image signal, both of said waveguides being attached to said spatula;

wherein said illumination light waveguide comprises a proximal end having an illumination light entry opening, and wherein said image waveguide comprises a proximal end having an image exit opening, wherein said illumination light entry opening and said image exit opening are arranged in an area of said coupling;

wherein said handle comprises, in said area of said coupling, an illumination light exit opening and an image entry opening which allow for said illumination light signal to couple into said illumination light waveguide from said handle, and for said image signal to couple out of said image waveguide;

wherein said laryngoscope further comprises a centering element which automatically aligns said image entry opening and said image exit opening precisely to each other; and wherein said spatula has a distal end, and said laryngoscope further comprising a gas sensor for measuring parameters of a gas mixture, said gas sensor being arranged at said distal end of said spatula.

14. The laryngoscope of claim 13, further comprising an evaluation unit arranged in said handle, said gas sensor being connected to said evaluation unit.

* * * * *